(12) United States Patent
Nardini et al.

(10) Patent No.: US 9,480,514 B2
(45) Date of Patent: Nov. 1, 2016

(54) CABLE TIE L-PIN

(71) Applicant: DePuy Synthes Products, Inc., Raynham, MA (US)

(72) Inventors: Reto Nardini, Grenchen (CH); Dieter Schmidli, Seewen (CH); Bruno Laeng, Horriwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 131 days.

(21) Appl. No.: 14/567,207

(22) Filed: Dec. 11, 2014

(65) Prior Publication Data

US 2015/0094779 A1    Apr. 2, 2015

Related U.S. Application Data

(62) Division of application No. 13/409,788, filed on Mar. 1, 2012, now Pat. No. 8,932,336.

(60) Provisional application No. 61/475,044, filed on Apr. 13, 2011.

(51) Int. Cl.
| | |
|---|---|
| *A61B 17/80* | (2006.01) |
| *A61B 17/84* | (2006.01) |
| *A61B 17/68* | (2006.01) |
| *A61B 17/00* | (2006.01) |

(52) U.S. Cl.
CPC .......... *A61B 17/844* (2013.01); *A61B 17/683* (2013.01); *A61B 17/80* (2013.01); *A61B 17/842* (2013.01); *A61B 2017/005* (2013.01); *A61B 2017/00955* (2013.01)

(58) Field of Classification Search
CPC .............. A61B 2017/681; A61B 2017/00508; A61B 2017/00517; A61B 2017/005
USPC ................................................... 606/64, 331
See application file for complete search history.

(56) References Cited

U.S. PATENT DOCUMENTS

| | | | | |
|---|---|---|---|---|
| 5,098,433 | A | * | 3/1992 | Freedland .............. A61B 17/68 606/60 |
| 5,735,875 | A | | 4/1998 | Bonutti et al. |
| 6,464,713 | B2 | * | 10/2002 | Bonutti .............. A61B 17/0401 606/232 |

(Continued)

FOREIGN PATENT DOCUMENTS

| | | |
|---|---|---|
| EP | 1920721 A2 | 5/2008 |
| WO | WO 02/09602 A1 | 2/2002 |
| WO | WO 2012/141813 | 10/2012 |

OTHER PUBLICATIONS

U.S. Appl. No. 61/475,044, filed Apr. 13, 2011, Nardini et al.

*Primary Examiner* — David Bates
(74) *Attorney, Agent, or Firm* — Baker & Hostetler LLP (57) ABSTRACT

A device for treating a bone includes (a) an elongate body sized and shaped for insertion into a bone and extending longitudinally from a proximal end to a distal end, the elongate body including a channel extending therethrough and a coating along an outer surface thereof, the coating adapted to absorb a selected frequency of light such that, when the selected frequency of light is applied thereto, portions of the coating melt to form a mass; and (b) a first anchor member slidably mountable over the elongate body and movable therealong from a first position at the proximal end of the elongate body to a second position adjacent a bone into which the elongate body has been inserted to cooperate with the mass to fix the elongate body to the bone.

18 Claims, 6 Drawing Sheets

(56) References Cited

U.S. PATENT DOCUMENTS

| | | |
|---|---|---|
| 6,620,185 B1 | 9/2003 | Harvie et al. |
| 7,361,179 B2 * | 4/2008 | Rousseau ............ A61B 17/683 606/281 |
| 8,230,555 B2 * | 7/2012 | Browne ................ B65D 63/12 24/16 PB |
| 8,425,574 B2 * | 4/2013 | Huebner ............ A61B 17/1728 606/281 |
| 8,932,336 B2 | 1/2015 | Nardini et al. |
| 2006/0282105 A1 | 12/2006 | Ford et al. |
| 2007/0270833 A1 | 11/2007 | Bonutti et al. |
| 2010/0211120 A1 * | 8/2010 | Bonutti ............ A61B 17/0401 606/86 R |

* cited by examiner

CABLE TIE L-PIN

CROSS REFERENCE TO RELATED APPLICATIONS

This application is a divisional of U.S. application Ser. No. 13/409,788, filed Mar. 1, 2012, which claims the benefit under 35 U.S.C. §119(e) of U.S. Provisional Application No. 61/475,044, filed on Apr. 13, 2011, the entire contents of each are expressly incorporated herein by reference thereto.

FIELD OF THE INVENTION

The present invention relates to devices for treating fractures and, in particular, relates an implant for fixing fractures.

BACKGROUND

Fractured bones are often fixed using bone fixation elements such as, for example, bone screws. A length of a bone screw selected for use in a particular procedure is generally based on a number of different factors such as, for example, a size of the bone to be fixed, the location on the bone to be fixed, and a desired angle of insertion of the bone screw. When standard bone screws are applied across a fracture, the threading pulls both fragments of bone in the same direction frustrating attempts to compress the fracture. To achieve compression in this case, a shaft screw is required so that the threading will engage only the fragment of bone on the far side of the fracture. All of these options require specialized screws in a variety of lengths and configurations increasing the materials required for these procedures. Further, bone screws often disengage from the driver complicating these procedures.

SUMMARY OF THE INVENTION

The present invention relates to a device for treating a bone, comprising an elongate body sized and shaped for insertion into a bone and extending longitudinally from a proximal end to a distal end, the elongate body including a channel extending therethrough and a coating along an outer surface thereof, the coating adapted to absorb a selected frequency of light such that, when the selected frequency of light is applied thereto, portions of the coating melt to form a mass and a first anchor member slidably mountable over the elongate body and movable therealong from a first position at the proximal end of the elongate body to a second position adjacent a bone into which the elongate body has been inserted to cooperate with the mass to fix the elongate body to the bone.

DETAILED DESCRIPTION

The present invention may be further understood with reference to the following description and the appended drawings, wherein like elements are referred to with the same reference numerals. The present invention relates to devices for treating fractures and, in particular, relates an implant for fixing fractures. Exemplary embodiments of the present invention describe a device including laser pin (L-pin) technology permitting portions of the device to be melted to hold it in place. For example, a distal end of the device may expand radially when melted to anchor the device within or against the bone while a cable tie mechanism is slid proximally along the device to apply compression across the fracture. It should be noted that the terms "proximal" and "distal" as used herein, are intended to refer to a direction toward (proximal) and away from (distal) a user of the device.

As shown in FIGS. 1-9, a device 100 according to an exemplary embodiment of the present invention comprises a body 102 sized and shaped for insertion into a fractured bone 10 and a plurality of anchor members 104 coupled thereto. The anchor members may be cable tie heads 104 which are pre-assembled along a proximal end 106 of the body 102 or mounted thereover during a surgical procedure. The body 102 may be inserted through the bone 10 and a distal end 108 thereof melted using L-pin technology. One cable tie head 104 may then be slid to a desired position along the body 102 adjacent an exterior of a near cortex 12 of the bone 10. A remaining portion of the body 102 may then be cut off proximally of the cable tie head 104 adjacent the bone 10 such that the remaining portion of the body 102 may be reused along with the remaining cable tie heads 104.

Figure 1:
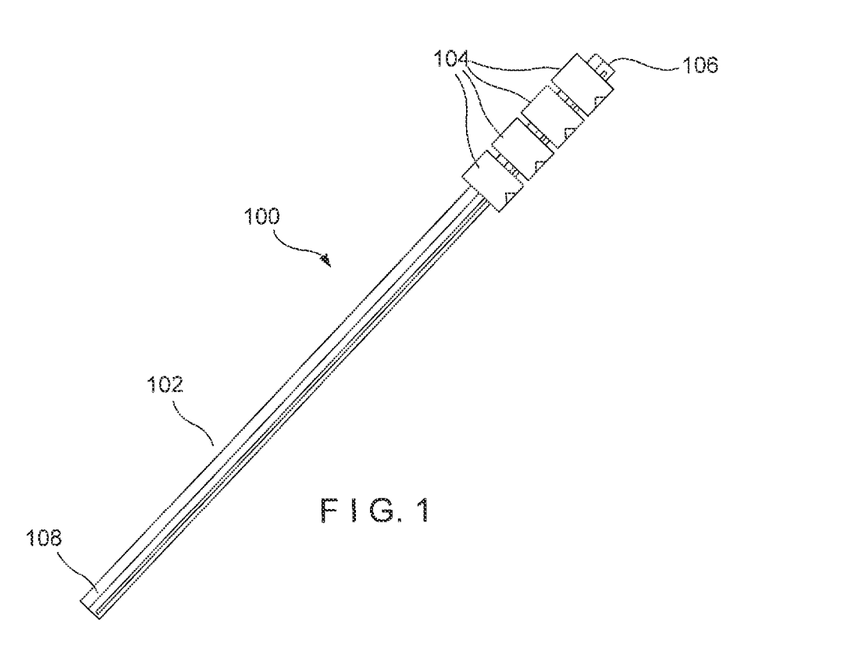
FIG. 1 shows a side view of a device according to an exemplary embodiment of the present invention.
Figure 2:
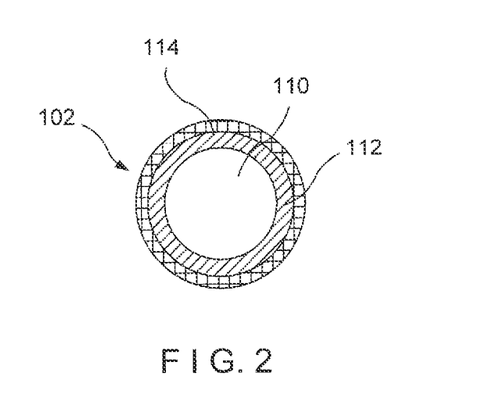
FIG. 2 shows a cross sectional view of a body of the device of FIG. 1.

As shown in FIGS. 1-2, the body 102 extends longitudinally from a proximal end 106 to a distal end 108 and includes a channel 110 extending therethrough. In one exemplary embodiment, the body 102 is substantially tubular with a diameter ranging from between 2 mm and 5 mm. It will be understood by those of skill in the art, however, that the body 102 may be any of a variety of shapes and sizes so long as the body 102 is configured for insertion through or into a portion of bone 10. In one use, the body 102 may be inserted into the bone 10 until the distal end 108 extends distally past a far cortex 14 of the bone 10. The channel 110 is sized and shaped to receive a laser fiber 116 or other laser device therein. The body 102 may be formed of, for example, a metallic core 112 coated with a thermoplastic polymer 114 including a pigment colored to absorb light of the wavelength produced by a laser to be used therewith. In an exemplary embodiment, the thermoplastic polymer coating 114 may extend around the entire exterior surface of the core 112. In an alternate embodiment, the thermoplastic polymer coating 114 may be applied over one or more portions of the core 112 while uncoated portions of the core 112 or portions coated with a clear polymer (or a polymer otherwise unaffected by the laser light) will not be melted when laser light is applied thereto.

The laser fiber 116 emits laser light radially from a distal tip thereof. Thus, when the laser fiber 116 is inserted into the channel 110 and is activated, the laser light at the distal tip melts the thermoplastic polymer 114 at the distal end 108 of the body 102. In particular, the colored pigment within the thermoplastic polymer coating 114 at the distal end 108 absorbs the laser energy, melting the polymer to form a mass 118 which hardens in an expanded shape as the mass 118 cools. Thus, the mass 118 prevents the distal end 108 of the body 102 from being moved proximally back into the bone 10.

One or more cable head tie heads 104 may be positioned along the proximal end 106 of the body 102 and individually movable therealong. Once the body 102 has been positioned in the bone 10 as desired and the distal end 108 has been melted to form the mass 118, a distal-most one of the cable tie heads 104a may be moved along the body 102 adjacent the near cortex 12 at a desired position along the body 102 to apply compression to the bone 10. The distal-most cable tie head 104a may be, for example, crushed over the body 102 to fix the distal-most cable tie head 104a to the body 102 at the desired position. A remaining length 120 of the body 102 extending proximally from the cable tie head 104a is then cut off and the distal-most cable tie head 104a adjacent the bone 10 is tightened to compress the fracture of the bone 10. In particular, the cable tie head 104a may be tightened by moving the distal-most cable tie head 104a distally along an implanted portion 122 of the body 102 compressing the fractured bone 10. The cable tie head 104a may be prevented from rotating about the body 102 during tightening of the distal-most cable tie head 104a via, for example, keyed portions of the body 102 and the cable tie head 104. For example, in one embodiment, the body 102 may have a non-circular cross section corresponding to a non-circular opening extending through the cable tie head 104. In another embodiment, the body 102 may include a teethed extending about an exterior surface thereof. Thus, once the distal-most cable tie head 104a is crushed thereover, an inner surface of the cable tie head 104a will engage the toothed surface preventing rotation of the cable tie head 104a relative to the body 102.

In a further embodiment, the body 102 has a thread along its length. The distal-most cable tie head 104a is advanced over the thread to apply an initial compression similarly to the other embodiments. The cable tie head 104a is then rotated about the thread to achieve a final compression, which can be to apply either more or less compression by moving the cable tie head 104a proximally or distally relative to the body. It is of course possible that the rotation can also be used to remove the cable tie head 104a completely from the body 102. After the cable tie head 104a is adjusted to a desired position, it may be, for example, crushed over the body 102 to fix it at that position.

The remaining length 120 and the remaining cable tie heads 104 may be reused. In one embodiment, the device includes four cable tie heads 104. It will be understood by those of skill in the art, however, that the device 100 may include any number of cable tie heads 104 depending on a number of times that the device 100 may be used. Similarly, a length of the body 102 may also vary depending on the number of times that the device 100 may be used. For example, the body 102 may have a length ranging from between 20 to 240 mm. Thus, the number of cable tie heads 104 may also correspond to the length of the body 102. It will be understood by those of skill in the art that although a plurality of cable tie heads 104 is specifically described, the device 100 may include one cable tie head 104.

Figure 3:
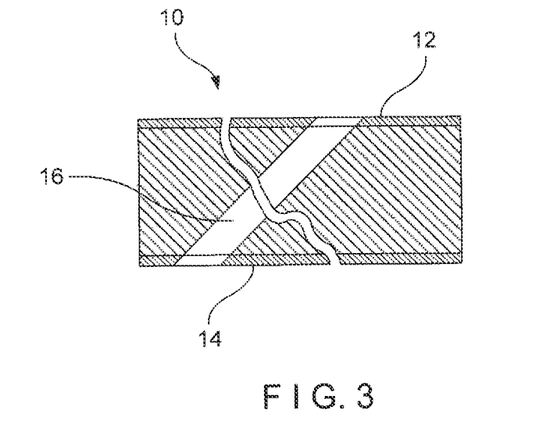
FIG. 3 shows a side view of a bone in which fractured portions are reduced and a hole drilled therethrough to accommodate the device of FIG. 1.
Figure 4:
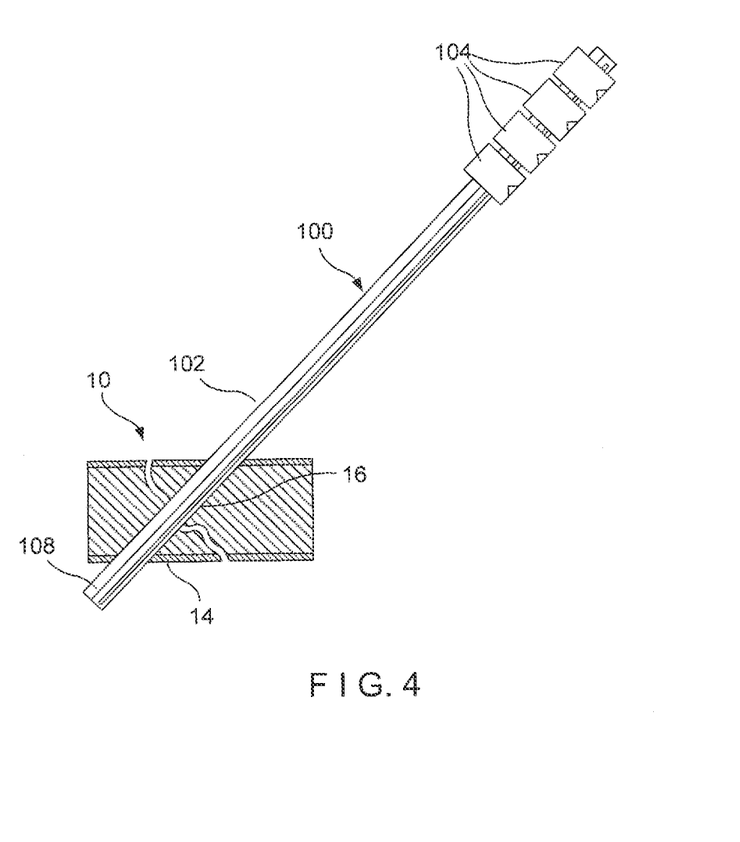
FIG. 4 shows a side view of the device of FIG. 1 inserted into the bone of FIG. 2.
Figure 5:
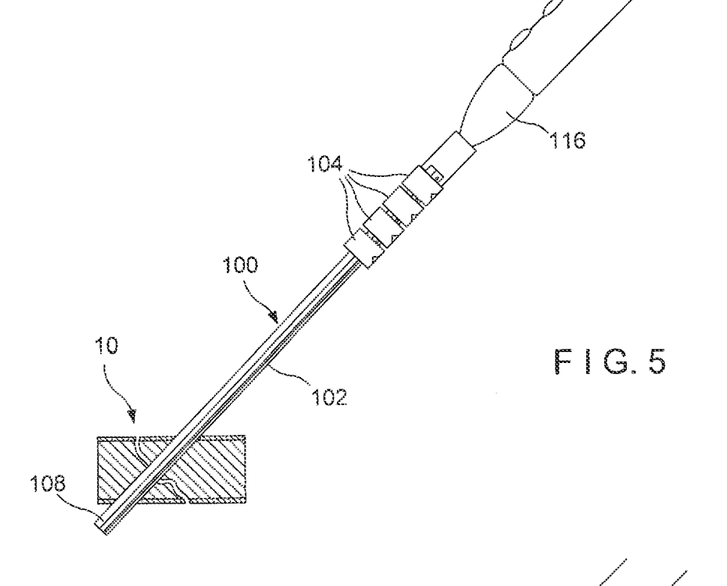
FIG. 5 shows a side view of a laser inserted into the device of FIG. 1.
Figure 6:
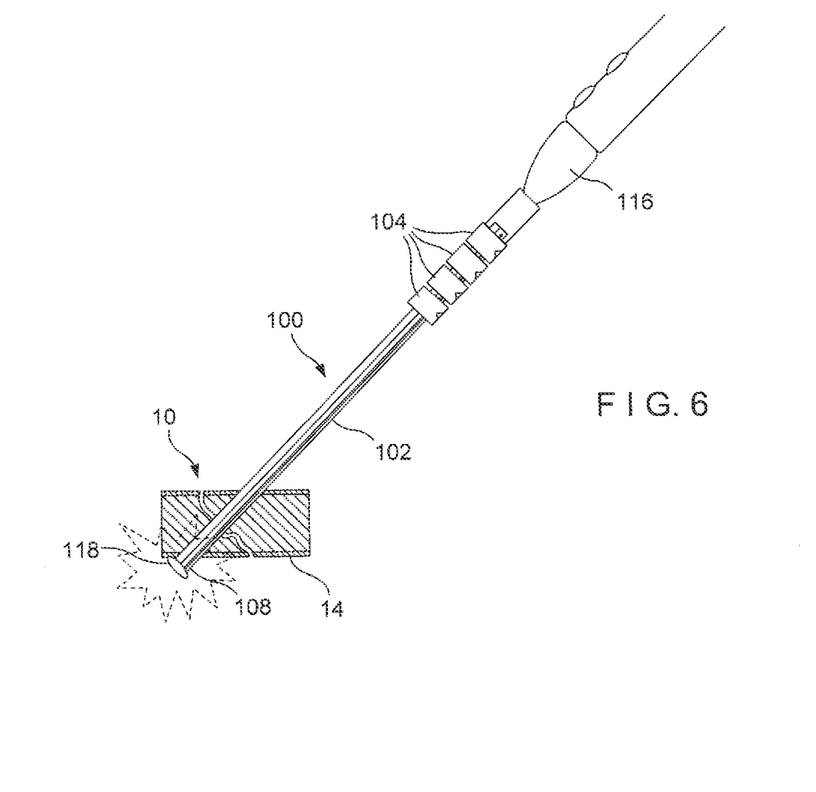
FIG. 6 shows a side view of the laser melting a distal end of the device of FIG. 1.

According to an exemplary surgical technique using the device 100, fractured portions of a bone 10 are reduced and a hole 16 is drilled therethrough along a desired path over which the body 102 is to be inserted into the bone 10 to fix the fractured portions, as shown in FIG. 3. The body 102 may then be inserted through the drilled hole 16, as shown in FIG. 4, until the distal end 108 of the device extends distally past a far cortex 14 (e.g., past an exterior surface of the far cortex 14) of the bone 10. As shown in FIG. 5, the laser 116 is then inserted through the channel 110 until a distal tip thereof is positioned radially within the distal end 108 of the body 102 and the laser 116 is activated to melt the distal end 108 forming the mass 118, as shown in FIG. 6. As described above, the mass 118 prevents the distal end 108 of the body 102 from being drawn proximally back into the bone 10.

Figure 7:
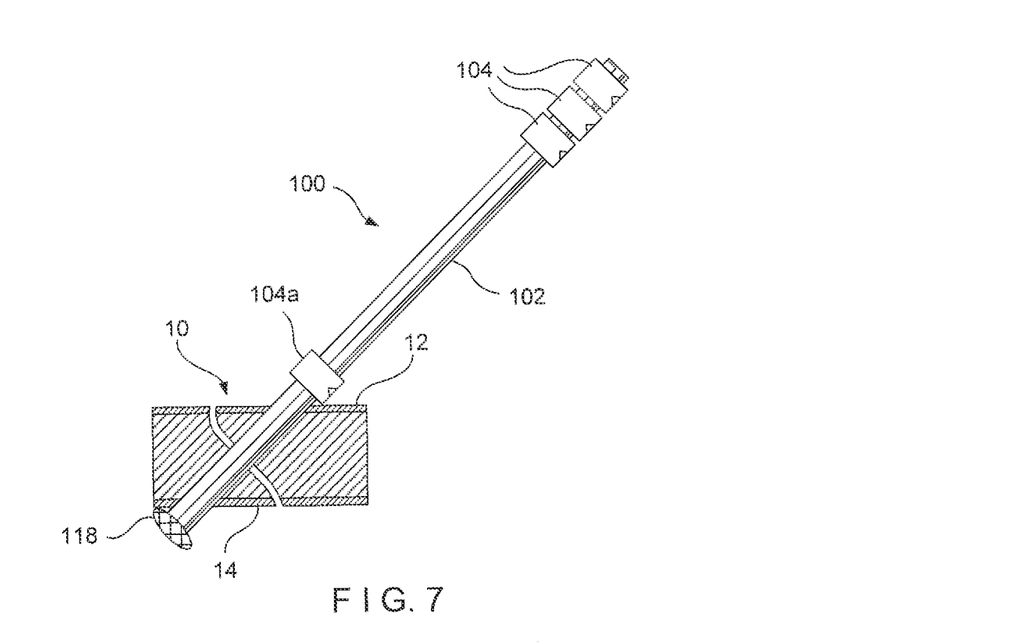
FIG. 7 shows a side view of a repositioned cable tie head of the device of FIG. 1.
Figure 8:
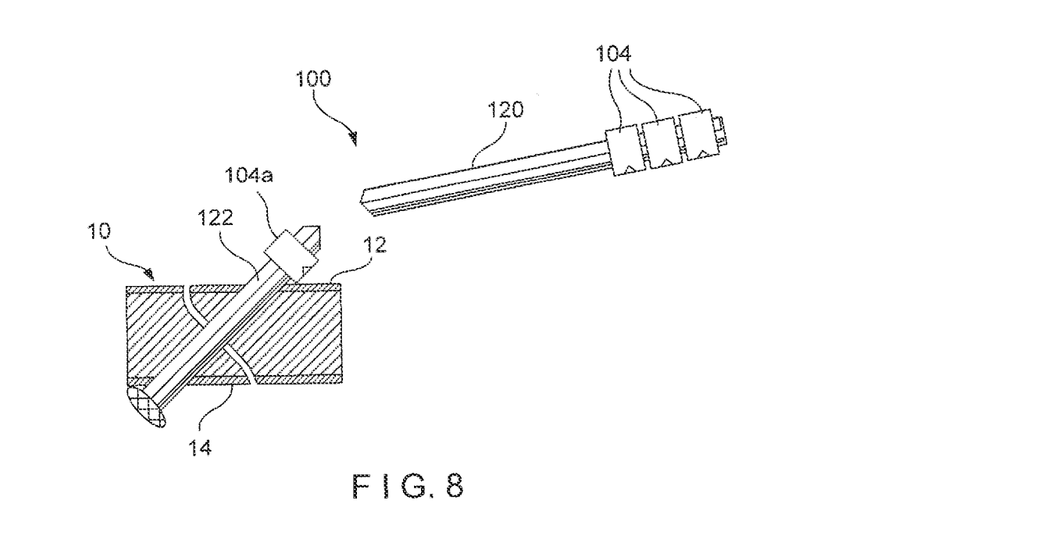
FIG. 8 shows a side view of a remaining portion cut off from an implanted portion of the device of FIG. 1.
Figure 9:
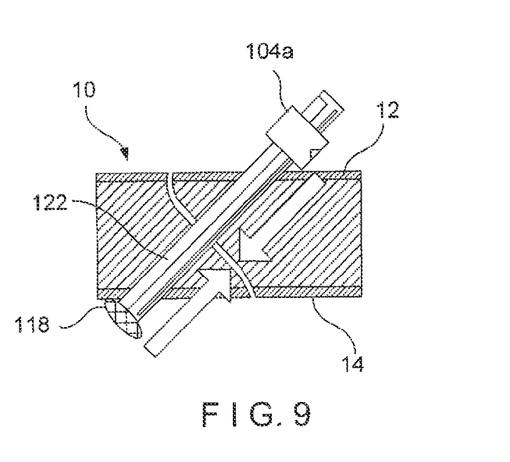
FIG. 9 shows a side view of the implanted portion of the device of FIG. 1.

The laser 116 is then removed from the device 100 and the distal-most cable tie head 104a is slid distally along the body 102 until it abuts an exterior surface of a near cortex 12 of the bone 10, as shown in FIG. 7. Once the distal-most cable tie 104a has been positioned along the body 102, as desired, a remaining length 120 of the body 102 extending proximally from the cable tie 104 is severed from the implanted portion 122, as shown in FIG. 8. The remaining cable tie heads 104 remain positioned along the proximal end 106 of the remaining length 120. The distal-most cable tie head 104a is then tightened, if desired, to achieve a desired compression of the bone 10. Since the mass 118 abuts the far cortex 14, tightening the distal-most cable tie head 104 (i.e., moving the distal-most cable tie head 104a distally relative to the implanted portion 122) compresses the bone 10, as shown in FIG. 9.

Figure 10:
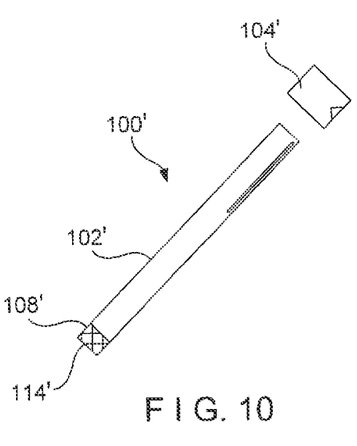
FIG. 10 shows a side view of a device according to an alternate embodiment of the present invention.

The remaining length 120 of the body 102 and the remaining cable tie heads 104 may be reused to fix other bones or other portions of the bone 10. The remaining length 120 and cable tie heads 104 may be used in the same manner, as described above, until a remaining length is insufficient to compress a bone and/or no more cable tie heads 104 remain. In an alternative embodiment, as shown in FIG. 10, a device 1 00' may be substantially similar to the device 100, described above, but may be configured for a single use. For example, a length of a body 102' may be selected to provide for a single compression of a bone and the device 100' may include a single cable tie head 104'. In addition, since the device 100' is suited for a single use, the body 102' may include a thermoplastic coating 114' along a distal end 108' only. It will be understood by those of skill in the art, however, that the thermoplastic coating 114' may extend along any portion or an entire exterior surface of the body 102'. For example, portions of the body 102' may be coated with a clear polymer (or a polymer otherwise unaffected by the laser light) to direct laser light to the distal end 108' such that a colored pigment within the thermoplastic coating 114' along the distal end 108' absorbs the laser energy, melting the polymer at the distal end 108' to form a mass which hardens in an expanded shape. The device 100' may be used in a manner substantially similar to the surgical technique described above. Specifically, the body 102' is inserted through a bone such that the distal end 108' extends distally beyond a far cortex thereof. The laser is then inserted through the body 102' and energy is applied thereto such that the pigmented polymer coating along the distal end 108' is melted to form a mass. The laser may then be removed and the cable tie head 104' moved distally along the body 102' to compress the bone, as desired. It will be understood by those of skill in the art, however, that the device 100' may not require a remaining length of the body 102' to be cut off from an implanted portion of the body 102' since a length of the body 102' may be specifically selected for a single use.

Alternatively, rather than being coated with the polymer material, the body 102' may be formed of a clear polymer material such as for example, polylactide or polycaprolactone, which may be either oriented or non-oriented. The polymer may include an additional expanding substance such as, for example, water in bubbles or Natron. The distal end 108' may include a laser absorbent material such as a colored pigment such that when the laser is applied to the body 102', the pigmented portion of the polymer is melted to form a mass. Since the body 102' is formed of the clear polymer material, which is unaffected by the laser energy, a laser applied to the body 102' will be directed to the pigmented portion at the distal end 1 08' such that the body 102' does not require a channel extending therethrough to receive the laser device. The colored pigment may be, for example, Indocyanine green or Blue No. 9.

Figure 11:
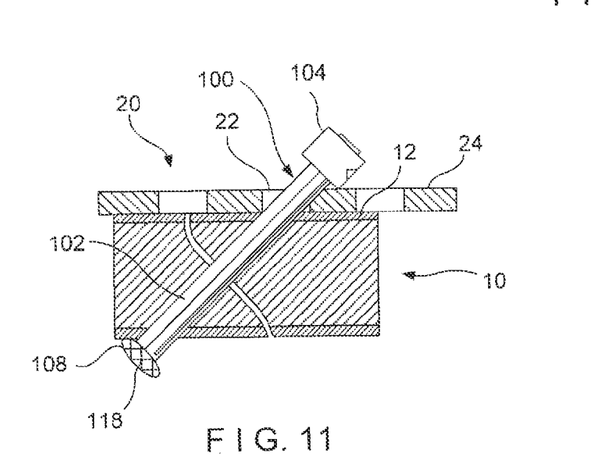
FIG. 11 shows a side view of the device of FIG. 1 used in conjunction with a bone plate.

According to a further exemplary embodiment, as shown in FIG. 11, the device 100 may be used in conjunction with a bone plate 20. The bone plate 20 is positioned along the near cortex 12 of the bone 10 in which fractured portions are reduced, and the device 100 is used in a manner substantially similar to the surgical technique described above. In particular, a hole may be drilled through an opening 22 of the bone plate 20 and the body 102 inserted therein, as described above. The distal end 108 is similarly melted to a mass 118 and the cable tie head 104 is moved proximally along the body 102. Rather than abutting a near cortex of the bone 10, however, the cable tie head 104 abuts a surface 24 of the bone plate 20. The cable tie head 104 may be similarly tightened to compress the fractured bone 10.

Figure 12:
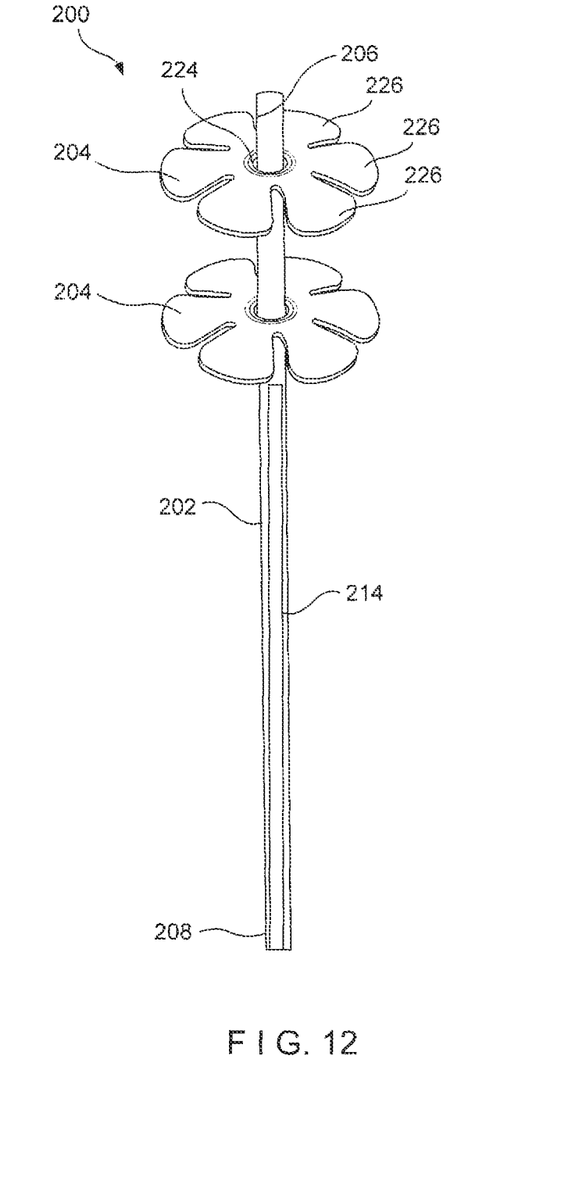
FIG. 12 shows a perspective view of a device according to another exemplary embodiment of the present invention.

As shown in FIG. 12, a device 200 may be substantially similar to the device 100, as described above, comprising a body 202 and a plurality of anchor members 204 coupled thereto and slidable therealong. Similarly to the device 100, the body 202 extends longitudinally from a proximal end 206 to a distal end 209 and includes a thermoplastic polymer coating 214 along a length thereof such that a laser device may melt the distal end 208, as described above. The anchor member 204, however, is not fixed to the body 202 at a desired position therealong via a cable tie mechanism, as described above in regard to the device 100. Rather, the anchor members 204 may be welded to the body 202 at a desired position therealong by melting the thermoplastic polymer coating 214 at the desired position.

The anchor member 204 may include an opening 224 extending therethrough for accommodating the body 202 and a plurality of radially extending flaps 226. The flaps 226 may be bent relative to one another such that when the anchor member 204 is positioned along a near cortex of the bone, the flaps 226 may be deformed to conform to a surface the of the near cortex. Although the anchor member 204 is specifically shown as a substantially planar element including radially extending flaps 226, it will be understood by those of skill in the art that the anchor member 204 may have any of a variety of shapes and sizes so long as the anchor member 204 is formed of a material that may be welded to the body 202 by melting the thermoplastic polymer coating 214 at a position corresponding to a position of the anchor member 204. For example, the anchor member 204 may be formed of a metal material.

The device 200 may be utilized in a manner substantially similar to the exemplary surgical technique described above with respect to the device 100. In particular, the body 202 is inserted into a bone until the distal end 208 extends distally beyond a far cortex thereof. A laser device is then inserted through a channel extending through the body 202 until a distal end of the laser device is positioned radially within the distal end 208 such that the distal end 208 may be melted to form a mass. Once the mass has been formed at the distal end 208, a distal-most one of the anchor members 204 is moved distally along the body 202 until it is pressed against the near cortex of the bone in a desired position along the body 202. The distal-most anchor member 204 should be pressed against the near cortex while the mass at the distal end 208 is pressed against the far cortex. The distal end of the laser device is positioned radially within the body 202 at the desired position corresponding to the distal-most anchor member 204. The laser device is activated to melt the thermoplastic polymer 214 at the desired position such that the anchor member 204 is welded thereto. A remaining length of the body 202 extending proximally from the distal-most anchor member 204 may be severed from an implanted portion thereof such that the remaining length may be reused to fix other bones or other portions of the bone, as discussed above in regard to the device 100.

It will be understood by those of skill in the art that the device 200 may include any number of anchor members 204 depending on a desired number of uses of the device 200 and a length of the elongate body 202 may be similarly selected for the desired number of uses. Alternatively, the device 200 may be configured for a single use, including a single anchor member 204 and a body 202 having a corresponding length.

It will be apparent to those skilled in the art that various modifications and variations can be made in the structure and the methodology of the present invention, without departing from the spirit or scope of the invention. For example, in any of the above described methods, the distal end of the body 102 may be located within a bone abutting an internal structure thereof. Thus, it is intended that the present invention cover the modifications and variations of this invention provided that they come within the scope of the appended claims and their equivalents.

What is claimed is:

1. A method for treating a fractured bone, comprising:
   inserting an elongate body of a bone fixation device through a bone such that a distal end of the elongate body extends distally past a far cortex of the bone, the elongate body extending longitudinally from a proximal end to the distal end, the elongate body including a channel extending therethrough and a coating adapted to absorb a selected frequency of light, the coating extending along an outer surface of the elongate body;
   inserting a light fiber through the channel of the elongate body until a distal tip of the light fiber is radially within the distal end of the elongate body;
   activating the light fiber such that the coating along the distal end of the elongate body melts to form a mass; and
   moving a first anchor member along the elongate body from a first position at the proximal end of the elongate body to a second position adjacent a near cortex of the bone to fix the elongate body to the bone.

2. The method of claim 1, further comprising reducing fractured portions of the bone and drilling a hole therethrough.

3. The method of claim 1, further comprising severing a proximal portion of the elongate body from a first implanted portion of the elongate body, the first implanted portion extending from the distal end to the first anchor member, the bone fixation device including a second anchor member, wherein a length of the proximal portion of the elongate body is sufficient to form a second implanted portion of the elongate body.

4. The method of claim 3, further comprising:
inserting the proximal portion of the elongate member into another portion of bone;
inserting the light fiber through the channel of the proximal portion until a distal tip of the light fiber is radially within a distal end of the proximal portion;
activating the light fiber such that the coating along the distal end of the proximal portion melts to form a mass; and
moving a second anchor member from the proximal end of the proximal portion to a position adjacent the another portion of bone to fix the proximal portion to the associated bone.

5. The method of claim 4, wherein the bone fixation device includes a third anchor member, wherein a length of the proximal portion is sufficient to form a third implanted portion.

6. The method of claim 1, further comprising tightening the first anchor member such that elongate body is moved proximally therethrough to compress fractured portions of the bone.

7. The method of claim 1, further comprising positioning a bone plate along the bone such that the elongate body is inserted through an opening of the bone plate.

8. The method of claim 1, further comprising welding the first anchor member to the elongate body in the second position by activating the laser device such that the coating along a portion of the elongate body radially within the first anchor member is melted.

9. The method of claim 1, further comprising crushing the first anchor member to positionally fix a position of the first anchor member with respect to the elongate body.

10. A method for treating a fractured bone, comprising:
inserting an elongate body of a bone fixation device through a bone such that a distal end of the elongate body extends distally past a far cortex of the bone, the elongate body extending longitudinally from a proximal end of the elongate body to the distal end, the elongate body including a first material adapted to absorb a selected frequency of light and a second material adapted to transmit the selected frequency of light, the first material being disposed at the distal end of the elongate body;
applying a laser to the elongate body;
activating the laser such that the first material of the elongate body melts to form a mass, and such that the second material does not melt; and
moving a first anchor member along the elongate body from a first position at the proximal end of the elongate body to a second position adjacent a near cortex of the bone to fix the elongate body to the bone.

11. The method of claim 10, further comprising applying the laser directly to the second material of the elongate body at the proximal end.

12. The method of claim 11, wherein the first material comprises a colored pigment and the second material comprises a polymer.

13. The method of claim 10, further comprising crushing the first anchor member to positionally fix a position of the first anchor member with respect to the elongate body.

14. The method of claim 10, further comprising reducing fractured portions of the bone and drilling a hole therethrough.

15. The method of claim 10, further comprising severing a proximal portion of the elongate body from a first implanted portion extending from the distal end to the first anchor member, the bone fixation device including a second anchor member, wherein a length of the proximal portion of the elongate body is sufficient to form a second implanted portion.

16. The method of claim 10, further comprising tightening the first anchor member such that elongate body is moved proximally therethrough to compress fractured portions of the bone.

17. The method of claim 10, further comprising positioning a bone plate along the bone such that the elongate body is inserted through an opening of the bone plate.

18. The method of claim 10, further comprising crushing the first anchor member to positionally fix a position of the first anchor member with respect to the elongate body.

* * * * *